(12) United States Patent
Himmelsbach et al.

(10) Patent No.: US 6,551,704 B2
(45) Date of Patent: *Apr. 22, 2003

(54) SELF-ADHESIVELY TREATED BACKING MATERIALS

(75) Inventors: Peter Himmelsbach, Buxtehude (DE); Peter Jauchen, Hamburg (DE); Andreas Albrod, Seevetal (DE); Arthur-Hugh Andrews, Kölln-Reisiek (DE); Klaus Keite-Telgenbüscher, Hamburg (DE); Reiner Leutz, Reinbek (DE); Christian Scharnhorst, Hetlingen (DE); Thorsten Stradt, Hamburg (DE); Andreas B. Kummer, Hamburg (DE); Sebastian Trotter, Buchholz (DE)

(73) Assignee: Beiersdorf AG, Hamburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 124 days.

(21) Appl. No.: 08/905,905

(22) Filed: Aug. 4, 1997

(65) Prior Publication Data

US 2001/0051482 A1 Dec. 13, 2001

(30) Foreign Application Priority Data

Aug. 6, 1996 (DE) ......................................... 196 31 422

(51) Int. Cl.[7] .................................................. B32B 7/12
(52) U.S. Cl. ........................ 428/343; 428/349; 428/355; 442/151
(58) Field of Search ................................ 428/343, 349, 428/355; 442/151

(56) References Cited

U.S. PATENT DOCUMENTS 5,453,319 A  9/1995  Gobran ........................ 428/355

FOREIGN PATENT DOCUMENTS

DE  4237252  5/1994  ............... C09J/7/02
EP  0443263  8/1991  ............... C09J/7/04

OTHER PUBLICATIONS

English–language Abstract of DE 42 37 252 (Oct. 13, 1994).

*Primary Examiner*—Elizabeth M. Cole
(74) *Attorney, Agent, or Firm*—Norris McLaughlin & Marcus

(57) ABSTRACT

Backing materials which have been given a self-adhesive treatment on at least one side, characterized in that the self-adhesive composition is a pressure-sensitive hotmelt adhesive composition which at a frequency of 0.1 rad/s has a dynamic-complex glass transition temperature of less than −3° C., preferably from −6° C. to −30° C. and, with particular preference, from −9° C. to −25° C., and their use, in particular, for producing medical products such as plasters, bandages or dressings.

20 Claims, No Drawings

SELF-ADHESIVELY TREATED BACKING MATERIALS

The invention relates to backing materials which have been treated to render them self-adhesive on at least one side, having been coated in whole or in part with a pressure-sensitive hotmelt adhesive composition, and to their use.

Strongly adhering orthopaedic bandages and other medical products are commonly coated over the whole of their area with a zinc-rubber adhesive composition. The sticking of such products to the skin entails, following their removal, marked skin irritation and mechanical stressing of the skin. Without recourse to auxiliary means, the bond cannot be detached without pain. In some cases there are allergic reactions. Furthermore, the adhesive compositions used often lead to a transfer of composition onto the skin.

The use of skin-friendly adhesive compositions such as acrylate adhesive compositions is out of the question because of their low shear stability and finger tack. Improvement through aftertreatment, especially crosslinking, is possible, although the result remains unsatisfactory as a whole. In addition, the bond strength to the backing of such systems, in the case of multiply dressings applied in circular form, is inadequate for a stable functional bandage. The proprioreceptive effect is less than that of systems with a zinc-rubber adhesive composition.

Other known adhesive systems based on conventional block copolymers are not skin-friendly, owing to the addition of excessive stabilizer, or because of the high cohesiveness have been found suitable to date only for industrial applications; or alternatively, they cannot be formulated for strong adhesion and sticking to the skin.

In the case of partial coating, the limited possibility for application of composition results in an inadequate bond strength, especially in the case of heavy backing materials.

The abovementioned adhesive compositions are pressure-sensitive self-adhesive compositions, where the compositions may be present in a carrier matrix for processing. The term carrier matrix is understood to refer to common organic or inorganic solvents or dispersion media.

Systems without a carrier matrix are referred to as 100% systems and are likewise not unknown. They are processed in the elastic or thermoplastic state. A common mode of processing is that of the melt.

Pressure-sensitive hotmelt adhesive compositions of this kind have also been described in the prior art. They are based on natural or synthetic rubbers and/or other synthetic polymers.

Because of their high level of hardness, sticking to the skin is a problem for such 100% systems.

An advantage of the 100% systems is that they avoid an operation of removing the carrier matrix, i.e. the auxiliary media, thereby raising the productivity of processing and at the same time reducing the expenditure on machinery and the energy costs. In addition, this reduces the occurrence of residues of the carrier matrix, which, in turn, favours a reduction in the allergenic potential.

It is also known to apply such self-adhesive compositions not only over the entire area but also in the form of a pattern of dots, for example by screen printing (DE-C 42 37 252), in which case the dots of adhesive can also differ in their size and/or distribution (EP-B 353 972), or by intaglio printing, in lines which interconnect in the longitudinal and transverse direction (DE-C 43 08 649).

The advantage of the patterned application is that the adhesive materials, given an appropriately porous backing material, are permeable to air and water and, in general, are readily redetachable.

A disadvantage of these products, however, is that if the area covered by the adhesive film, which per se is impermeable, is too large there is a corresponding reduction in the permeability to air and water vapour, and the consumption of adhesive composition rises, and also, if the area covered by the adhesive film is small, the adhesion properties suffer, i.e. the product is detached too readily from the substrate, especially in the case of heavy, textile backing materials.

The object of the invention, therefore, was to avoid the disadvantages known from the prior art and also to provide a backing material which is self-adhesive on at least one side and which owing to its treatment, i.e. to the properties of the adhesive composition, the form of application and the inherent properties of the backing material, can be used functionally for various fixing tasks, especially for medical products.

This object is achieved by a backing material which has been given a self-adhesive treatment on at least one side, the self-adhesive composition being a pressure-sensitive hotmelt adhesive composition which at a frequency of 0.1 rad/s has a glass transition temperature of less than $-3°$ C., preferably from $-6°$ C. to $-30°$ C. and, with particular preference from $-9°$ C. to $-25°$ C.

The adhesive composition is preferably based on block copolymers, especially A-B or A-B-A block copolymers or mixtures thereof. The hard phase A is above all polystyrene or its derivatives and the soft phase B is ethylene, propylene, butylene, butadiene, isoprene or mixtures thereof, in which case particular preference is given to ethylene and butylene or mixtures thereof. However, polystyrene blocks may also be present in the soft phase B in an amount of up to 20% by weight. The overall proportion of styrene in the polymer, however, is always less than 35% by weight. Preference is given to styrene contents of between 5% by weight and 30% by weight, since a lower styrene content makes the adhesive composition smoother.

The controlled blending of diblock and triblock copolymers is particularly advantageous, preference being given to a proportion of diblock copolymers of less than 80% by weight.

In one advantageous embodiment the pressure-sensitive hotmelt adhesive composition has the following composition:

from 10% by weight to 90% by weight of block copolymers, from 5% by weight to 80% by weight of tackifiers such as oils, waxes, resins and/or mixtures thereof, preferably mixtures of resins and oils, less than 60% by weight of plasticizers, less than 15% by weight of additives, and less than 5% by weight of stabilizers.

The oils, waxes and resins used as tackifiers are preferably hydrocarbon oils, waxes and resins, the consistency of the oils—such as paraffinic hydrocarbon oils—or of the waxes—such as paraffinic hydrocarbon waxes—accounting for their favourable effect on bonding to the skin. Plasticizers used are long-chain fatty acids and/or their esters. These additions serve to establish the adhesion properties and the stability.

Filling the adhesive composition with mineral fillers is possible.

The pressure-sensitive hotmelt adhesive composition has a softening point of more than $70°$ C., preferably from $95°$ C. to $120°$ C.

Stringent requirements in terms of the adhesion properties are placed in particular on medical products, for example an orthopaedic dressing. For ideal use the self-adhesive composition should possess a high tack. There should be functionally appropriate bond strength to the skin and to the reverse of the backing. So that there is no slipping of the plies, the self-adhesive composition is also required to have a high shear strength.

By the controlled reduction in the glass transition temperature of the self-adhesive composition, which is essential to the invention and occurs as a result of the selection of the tackifiers, the plasticizers, the polymer molecule size and the molecular distribution of the starting components, the required, functionally appropriate bonding to the skin and to the reverse of the backing is achieved. The high shear strength of the self-adhesive composition which is employed here is obtained by virtue of the high cohesiveness of the block copolymer. The good tack is a result of the range of tackifiers and plasticizers employed.

Product properties such as tack, glass transition temperature and shear stability can be quantified readily using a dynamo-mechanical frequency measurement. In this case, use is made of a rheometer controlled by shearing stress.

The results of this measurement method give information on the physical properties of a substance by taking into account the viscoelastic component. In this instance, at a preset constant temperature, the hotmelt pressure-sensitive adhesive is set in oscillation between two plane-parallel plates with variable frequencies and low deformation (linear viscoelastic region). Via a pickup control unit, with computer assistance, the quotient (Q=tan δ) between the loss modulus (G", viscous component) and the storage modulus (G', elastic component) is determined. A high frequency is chosen for the subjective sensing of the tack, and a low frequency for the shear strength.

A high numerical value denotes better tack and poorer shear stability.

The complex-dynamic glass transition point is the point of transition from the amorphous to the viscoelastic region. It corresponds to the maximum of the temperature function at a given frequency.

$$Q=\tan \delta=G''/G'$$

| Designation | $T_G$ low frequency | Shear stability low frequency/RT | Tack high frequency/RT |
|---|---|---|---|
| Hotmelt PSA A | −12 ± 2° C. | tan δ = 0.08 ± 0.03 | tan δ = 0.84 ± 0.03 |
| Hotmelt PSA B | −9 ± 2° C. | tan δ = 0.22 ± 0.03 | tan δ = 1.00 ± 0.03 |

Preference is given in accordance with the invention to pressure-sensitive hotmelt adhesive compositions for which the ratio of the viscous component to the elastic component at a frequency of 100 rad/s at 25° C. is greater than 0.7, or to pressure-sensitive hotmelt adhesive compositions where the ratio of the viscous component to the elastic component at a frequency of 0.1 rad/s at 25° C. is less than 0.4, preferably between 0.35 and 0.02 and, with particular preference, between 0.3 and 0.1.

It is also advantageous, especially with use for medical products, if the pressure-sensitive hotmelt adhesive composition is applied partially to the backing material, for example by halftone printing, thermal screen printing or intaglio printing, because backing materials which have been self-adhesively treated in a continuous applied line induce, on application, mechanical irritations of the skin.

The partial application makes it possible, through controlled channels, to dissipate the trans-epidermal water loss and improves the removal of sweat from the skin in vapour form, especially when the backing materials used are permeable to air and water vapour. By this means the skin irritations induced by accumulations of body fluids are avoided. The dissipation channels set up enable fluids to be conducted away even when a multiply dressing is used.

Preference is given to application in the form of polygeometric domes, especially those where the ratio of diameter to height is less than 5:1. Printed application of other forms and patterns on the backing material is also possible, for example a printed pattern in the form of alphanumeric character combinations or patterns such as matrices, stripes and zigzag lines.

In addition, they can also be sprayed on, for example, producing a more or less irregularly applied pattern. The self-adhesive composition can be distributed uniformly over the backing material; alternatively, it can also be applied with varying thickness or density as appropriate for the function of the product.

The principle of thermal screen printing consists in the use of a rotating, heated, seamless, drum-shaped perforated, cylindrical screen which is fed via a nozzle with the pressure-sensitive hotmelt adhesive composition. A specially shaped nozzle lip (circular or square doctor blade) presses the self-adhesive composition, which is fed in via a channel, through the perforation of the screen wall and onto the backing web that is conveyed past it. This backing web is guided by means of a counter-pressure roller against the external jacket of the heated screen drum at a rate which corresponds to the peripheral speed of the rotating screen drum.

In this context, the formation of the small domes of adhesive takes place by the following mechanism:

The pressure of the nozzle doctor blade conveys the self-adhesive composition through the screen perforation onto the backing material. The size of the domes formed is determined by the diameter of the screen perforation. The screen is lifted from the backing in accordance with the rate of transportation of the backing web (rotary speed of the screen drum). As a consequence of the high adhesion of the self-adhesive composition and the internal cohesion of the hotmelt, the limited supply of pressure-sensitive hotmelt adhesive composition in the perforations is drawn in sharp definition from the base of the domes that is already adhering to the backing and is conveyed by the blade pressure onto the backing. After the end of this transportation, the more or less highly curved surface of the dome forms over the pre-defined base area in dependence on the rheology of the pressure-sensitive hotmelt adhesive composition. The ratio of height to base of the dome depends on the ratio of the perforation diameter to the wall thickness of the screen drum and on the physical properties (flow behaviour, surface tension and contact angle on the backing material) of the self-adhesive composition.

In the case of the screen in thermal screen printing, the web-to-hole ratio can be less than 2:1, preferably less than or equal to 1:1.

The above described mechanism of formation of the domes preferably requires backing materials that are absorbent or at least wettable by pressure-sensitive hotmelt adhesive composition. Non-wetting backing surfaces must be pretreated by chemical or physical methods. This can be effected by additional measures such as corona discharge, for example, or by coating with substances which improve wetting.

Using the printing technique indicated it is possible to lay down the size and shape of the domes in a defined manner.

The bond strength values which are relevant for use and which determine the quality of the products formed are within very narrow tolerances in the case of proper coatings. The base diameter of the domes can be chosen from 10 µm to 5000 µm, the height of the domes from 20 µm to about 2000 µm, preferably from 50 µm to 1000 µm, the low-diameter range being intended for smooth backings and the range of greater diameter and greater dome height being intended for rough or highly porous backing materials.

The positioning of the domes on the backing is laid down in a defined manner by the geometry of the applicator unit, for example the gravure or screen geometry, which can be varied within wide limits. With the aid of the parameters indicated it is possible, by way of adjustable variables, to establish with very great precision the desired profile of properties of the coating, harmonized with various backing materials and uses.

The backing material is preferably coated at a rate of more than 2 m/min, more preferably from 20 to 100 m/min, the chosen coating temperature being greater than the softening temperature.

The pressure-sensitive hotmelt adhesive composition can be applied to the backing material with a weight per unit area of more than 15 g/m$^2$, preferably between 70 g/m$^2$ and 300 g/m$^2$ and, with very particular preference between 90 g/m$^2$ and 160 g/m$^2$.

The percentage area that is coated with the hotmelt pressure-sensitive adhesive composition should be at least 20% and can range up to about 95%, for a specific product preferably from 40% to 60% and from 70% to 95%. This can be achieved, if desired, by means of multiple application, with the possible use if desired of adhesive compositions having different properties.

The self-adhesively treated backing material exhibits a bond strength to the reverse of the backing of at least 1.5 N/cm, in particular a bond strength of between 2.5 N/cm and 5 N/cm. Higher bond strengths may be achieved on other substrates.

The combination of the self-adhesive composition and the partial coating on the one hand ensures a reliable bond, in particular of the medical product to the skin; on the other hand, allergic or mechanical skin irritations, at least those which are visually perceptible, are ruled out, even in the case of use extending over a number of days.

The epilation of corresponding body regions and the transfer of composition to the skin are negligible owing to the high cohesiveness of the adhesive, since the adhesive is not anchored to skin and hair; rather the anchorage of the adhesive composition to the backing material, at up to 12 N/cm (sample width), is very good, especially for medical applications.

Because of the intended breakage points that have been formed in the coating, layers of skin are no longer displaced with one another or against one another in the course of detachment. The non-displacement of the layers of skin and the relatively low level of epilation lead to an unprecedented degree of painlessness in such systems with strong adhesion. In addition, the individual bio-mechanical control of bond strength, which exhibits a demonstrable reduction in the bond strength of the self-adhesively treated backing materials, assists the redetachability. The applied dressing shows good proprioreceptive effects.

Depending on the backing material and its temperature-sensitivity, the self-adhesive composition can be applied directly or can be applied first to an auxiliary support and then to the ultimate backing. In addition, subsequent calendering of the coated product and/or pretreatment of the backing, such as corona irradiation, for better anchorage of the adhesive layer, can be advantageous.

Suitable backing materials are all rigid and elastic sheet-like structures of synthetic and natural raw materials. Preference is given to backing materials which, following the application of the adhesive composition, can be employed in such a way that they fulfill the characteristics of a functional bandage. Examples are textiles such as wovens, knits, lays, nonwovens, laminates, nets, films, foams and papers. In addition, these materials can be pretreated or aftertreated. Common pretreatments are corona and hydrophobicization; customary aftertreatments are calendering, thermal conditioning, laminating, punching and covering.

The coated backing material can have an air permeability of greater than 1 cm$^3$/(cm$^{2*}$s), preferably greater than 15 cm$^3$/(cm$^{2*}$s) and, with particular preference, greater than 70 cm$^3$/(cm$^{2*}$s), and a water vapour permeability of greater than 500 g/(m$^{2*}$24 h), preferably greater than 1000 g/(m$^{2*}$24 h) and, with particular preference, greater than 2000 g/(m$^{2*}$24 h).

Furthermore, the coated backing material even in an assembly of plies can still have an air permeability of 1 cm$^3$/(cm$^{2*}$s) and a water vapour permeability of 500 g/(m$^{2*}$24 h).

Finally, the self-adhesively treated backing material can be covered after application or provided with a wound pad or with padding.

It is particularly advantageous that the self-adhesively treated backing material can be sterilized, preferably with γ (gamma) radiations. Consequently, particular suitability for subsequent sterilization is possessed by block copolymer-based pressure-sensitive hotmelt adhesive compositions which contain no double bonds. This applies in particular to styrene-butylene-ethylene-styrene block copolymers or styrene-butylene-styrene block copolymers. In the course of such treatment the adhesive properties are not subject to any changes significant for their use.

The above mentioned properties of the backing material that has been self-adhesively treated on at least one side suggests in particular its use for medical products, especially plasters, medical fixings, wound covers, and also orthopaedic or phlebological bandages and dressings.

In addition, the use of a self-adhesively treated backing material is also suitable for reversible technical fixings which can be detached without damage to the substrate (for example paper, plastics, glass, textiles, wood, metals or minerals).

The intention below is to illustrate a self-adhesively treated backing material according to the invention by means of a number of examples, without wishing unnecessarily to restrict the invention.

EXAMPLE 1

In accordance with the invention a nonelastic self-adhesive dressing was prepared which on the basis of its properties, described below, can be used as a functional tape bandage, the functional bandaging technique being guided by the anatomy and by the biomechanics. The dressing used for this type of bandage consisted of a nonelastic cotton woven fabric with a breaking strength of more than 60 N/cm and a breaking extension of less than 20%.

The self-adhesive composition was applied to the backing by thermal screen printing, and was a hotmelt self-adhesive mass. This pressure-sensitive hotmelt adhesive composition had the following composition:

an A-B/A-B-A block copolymer consisting of hard and soft segments, with a ratio of A-B-A to A-B of 3:7 and a styrene content in the polymer of 30 mol-%; the proportion of the adhesive composition is 64% by weight (Kraton G)

a paraffinic hydrocarbon wax with a proportion in the adhesive composition of 32% by weight hydrocarbon resins with a proportion of 3.5% by weight (Super Resin HC 140)

An antioxidant with a proportion of less than 0.5% by weight (Irganox).

The components employed were homogenized at 175° C. in a thermal mixer.

The softening point of this adhesive composition was about 95° C. (DIN 52011), and the adhesive composition had a viscosity of 2400 mPas at 150° C. (DIN 53018, Brookfield DV II, spindle 21). By the abovementioned method the glass transition was −10° C.

Direct coating took place at a rate of 50 m/min and at a temperature of 120° C. The backing material was coated in dot formation with 120 g/m², using a 25 mesh screen with a thickness of 300 μm.

The dressing produced by this process exhibited reversible detachment from the skin and good permeability to air and water vapour. Because of the high shear stability of the hotmelt pressure-sensitive adhesive, sufficient stabilization and a good proprioreceptive effect were found. No skin irritations and a negligible degree of epilation were observed when the dressing had been removed.

EXAMPLE 2

By virtue of the disclosed invention it was possible to avoid the need to recover the solvent, which is often necessary, in an environmentally compatible manner, such recovery being cost-intensive and leading to high expenditure on machinery.

So, a dressing was coated by thermal screen printing with 160 g/m² of an adhesive composition based on a block copolymer.

The block copolymer was a styrene-ethylene-butylene-styrene block copolymer to which paraffinic hydrocarbon wax had been added. The ratio was one part of polymer to one part of paraffinic hydrocarbon. To this mixture there was added 10% of polystyrene resin (Amoco 18240). The adhesive contained one per cent of Irganox, an antioxidant (n-octadecyl β-(3,5,di-t-butyl-4-hydroxyphenyl)-proprionate), and other hydrocarbon resins and fatty acid esters, which were present only in small amounts in the overall adhesive. The softening point of this adhesive composition was about 100° C. (DIN 52011) and the glass transition temperature, determined by the abovementioned method, was −6° C.

The high amount of composition applied was applied using a 14 mesh screen with an open area of 51%. The use of the large coating dots made it possible to obtain good adhesion to the backing and clean cutting. In accordance with the invention, the adhesive composition was skin-compatible and showed good adhesion to the skin and to the reverse of the backing.

The dressing produced in this way, even in a multiply bandage, was permeable to air (more than 15 cm³/(cm²*s) and permeable to water vapour (more than 1500 g/(m²*24 h)).

The elastic adhesive dressing was used for compression, support and relief bandages, where the high initial and long-term bond strength and the shear force were advantageous. The shapeability and impression obtained by the user were improved as a result of the partial application of the adhesive composition.

EXAMPLES 3–5

The table below indicates clearly further examples of different, coated backing materials and the results obtained with the backing materials coated as indicated.

| Designation | Example 3 | Example 4 | Example 5 |
|---|---|---|---|
| Backing material | elastic cotton woven fabric | rigid cotton woven fabric | rigid rayon woven fabric |
| screen (mesh and thickness) | 14 M/ 450 μm | 14 M/ 300 μm | 25 M/ 300 μm |
| glass transition temp. in ° C. (hotmelt self-adhesive PSA) | −16 ± 2° C. | −16 ± 2° C. | −16 ± 2° C. |
| Tack (hotmelt self-adhesive PSA) | tan δ = 0.93 ± 0.03 | tan δ = 0.93 ± 0.03 | tan δ = 0.93 ± 0.03 |
| Shear stability (hotmelt self-adhesive PSA) | tan δ = 0.10 ± 0.03 | tan δ = 0.10 ± 0.03 | tan δ = 0.10 ± 0.03 |
| Composition applied in g/m² | 140 | 125 | 82 |
| Bond strength to steel in N/cm | 8.5 | 10.3 | 6.5 |
| Bond strength to the reverse of the backing in N/cm | 2.3 | 3.5 | 2.5 |
| Air permeability in cm³/(cm²*s) | 96 | 67 | 103 |
| Water permeability in g(m²*24 h) | 2500 | 2100 | 2800 |
| Transfer to skin | no | no | no |
| Instances of skin incompatibility/irritation | none | none | none |

What is claimed is:

1. Backing materials having a self-adhesive composition on at least one side, wherein said self-adhesive composition is a pressure-sensitive hotmelt adhesive composition which at a frequency of 0.1 rad/s has a dynamic-complex glass transition temperature of less than −30° C., the overall proportion of styrene in the polymer is less than 35% by weight and the pressure-sensitive hotmelt adhesive composition consists of

| | |
|---|---|
| from 10% by weight to 75% by weight | of block copolymers, |
| from 5% by weight to 80% by weight | of tackifiers, |
| less than 60% by weight | of plasticizers, |
| less than 15% by weight | of additives, and |
| less than 5% by weight | of stabilizers. |

2. Backing material according to claim 1, wherein the adhesive composition is formulated of A-B or A-B-A block copolymers, or mixtures thereof, in which phase A is polystyrene or its derivatives and phase B is ethylene, propylene, butylene, butadiene, isoprene or mixtures thereof.

3. Backing material according to claim 1, wherein the tackifiers are hydrocarbon oils, waxes or resins.

4. Backing material according to claim 1, wherein non-adhesive substances are admixed to the pressure-sensitive hotmelt adhesive composition.

5. Backing material according to claim 1, wherein the ratio of the loss modulus (viscous component) to the storage modulus (elastic component) of the pressure-sensitive hotmelt adhesive composition at a frequency of 100 rad/s at 25° C. is greater than 0.7.

6. Backing material according to claim 1, wherein the ratio of the loss modulus (viscous component) to the storage modulus (elastic component) of the pressure-sensitive hot-melt adhesive composition at a frequency of 0.1 rad/s at 25° C. is less than 0.40.

7. Backing material according to claim 1, wherein the self-adhesive composition is applied partially.

8. Backing material according to claim 1, wherein the pressure-sensitive hotmelt adhesive composition is applied by halftone printing, thermal screen printing or intaglio printing.

9. Backing material according to claim 1, wherein the self-adhesive composition is applied in the form of polygeometric domes to the backing material.

10. Backing material according to claim 1, wherein the self-adhesive composition is coated on the backing material with a weight per unit area of more than 15 g/m$^2$.

11. Backing material according to claim 1, wherein the self-adhesive composition is applied with an areal coverage of from 20% to 95%.

12. Backing material according to claim 1, wherein the self-adhesively treated backing material has a bond strength to the reverse of the backing of at least 1.5 N/cm.

13. Backing material according to claim 1, wherein the coated backing material has an air permeability of greater than 1 cm$^3$ (cm$^{2*}$s).

14. Backing material according to claim 1, wherein the coated backing material has a water vapour permeability of greater than 500 g/(m$^{2*}$24 h).

15. Backing material according to claim 1, wherein the backing material is pretreated.

16. Backing material according to claim 1, wherein the self-adhesively treated backing material, following application, is covered or is provided with a wound pad or with padding.

17. Backing material according to claim 1, wherein the self-adhesively treated backing material can be sterilized.

18. Backing material according to claim 1 applied to medical products selected from the group consisting of plasters, medical fixings, wound coverings, orthopaedic bandages, phlebological bandages and dressings.

19. Reversible technical fixings which can be detached without damage to the substrate comprising a backing material according to claim 1.

20. Backing material according to claim 17, wherein said backing is sterilizable by γ (gamma) radiation.

* * * * *

UNITED STATES PATENT AND TRADEMARK OFFICE
CERTIFICATE OF CORRECTION

PATENT NO. : 6,551,704 B2
DATED : April 22, 2003
INVENTOR(S) : Himmelsbach et al.

It is certified that error appears in the above-identified patent and that said Letters Patent is hereby corrected as shown below:

Column 8,
Line 37, "-30º C" should read -- -3º C --.

Signed and Sealed this

Third Day of August, 2004

JON W. DUDAS
*Acting Director of the United States Patent and Trademark Office*